United States Patent
Liao et al.

(10) Patent No.: US 7,767,445 B2
(45) Date of Patent: Aug. 3, 2010

(54) POROUS CHAMBER FOR TISSUE CULTURE IN VIVO

(75) Inventors: Chun-Jen Liao, Taipei (TW); Yu-Ju Lin, Luo Dung Village (TW); Chin-Fu Chen, Taipei (TW); Ken-Yuan Chang, Hsin Chu (TW); Shu-Fang Chiang, Hsin Chu (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 11/808,117

(22) Filed: Jun. 6, 2007

(65) Prior Publication Data

US 2008/0026455 A1 Jan. 31, 2008

Related U.S. Application Data

(63) Continuation of application No. 10/214,587, filed on Aug. 9, 2002, now abandoned.

(51) Int. Cl.
*C12M 1/14* (2006.01)
*C12M 3/04* (2006.01)

(52) U.S. Cl. .................................. 435/299.1

(58) Field of Classification Search ............... 435/299.1
See application file for complete search history.

(56) References Cited

U.S. PATENT DOCUMENTS

| 5,686,091 A | 11/1997 | Leong et al. |
| 5,795,591 A | 8/1998 | Lee et al. |
| 5,863,531 A * | 1/1999 | Naughton et al. ........... 424/93.7 |
| 6,537,567 B1 * | 3/2003 | Niklason et al. ............ 424/423 |

OTHER PUBLICATIONS

Kierszenbaum AL. 2000. The 26S proteasome: ubiquitin-mediated proteolysis in the tunnel. Mol Reprod Devel 57: 109-110.

* cited by examiner

*Primary Examiner*—Walter D Griffin
*Assistant Examiner*—Lydia Edwards
(74) *Attorney, Agent, or Firm*—Birch, Stewart, Kolasch & Birch, LLP (57) ABSTRACT

A porous chamber for tissue culture in vitro. The porous chamber includes a main body made of porous biologically absorbable polymer material, comprising an inner surface surrounding a hollow cavity, the hollow cavity having an aperture opened at an upper surface of the main body, wherein the aperture is communicated with outside of the main body for seeding tissue blocks in the hollow cavity, and an upper cover passing through the upper surface of the main body to seal the aperture to prevent the tissue blocks from outflowing.

12 Claims, 8 Drawing Sheets

FIG. 9

POROUS CHAMBER FOR TISSUE CULTURE IN VIVO

This application is a Continuation of application Ser. No. 10/214,587, filed on Aug. 9, 2002 now abandoned and for which priority is claimed under 35 U.S.C. §120; and this application claims priority of application Ser. No. 09,013, 0491 filed in Taiwan, R.O.C. on Dec. 10, 2001 under 35 U.S.C. §119; the entire contents of all are hereby incorporated by reference.

BACKGROUND OF THE INVENTION

1. Field of the Invention

The present invention relates to a method for tissue culture in vitro, more particularly, a method that places tissue blocks gathered into the hollow cavity of a porous dissoluble chamber, and then, by providing nutrients, the tissue blocks are to grow three-dimensionally toward the surrounding pores of the porous scaffold, thus new tissue is to be proliferated.

2. Description of the Prior Art

When human tissue is destructed or organs are destructed beyond repair due to accidents, aging or diseases, patients are often forced to experience limb dysfunctions or life-threatening crises, situations that may further lead to tremendous burden and loss for families and societies. Therefore, researchers indefatigably endeavor to seek appropriate tissue or organs for repair and replacement. In recent years, with the advancement of biotechnology, the biomedical material and culture technique for tissue cells are already combined to form a new field of research called tissue engineering. It is to be expected in the near future that, through the regeneration technology in the field of tissue engineering, the damaged tissue or organs can be repaired in vitro, or brand new tissue or organs can be produced in vitro to replace the damaged portions, thus the health of patients is recovered, and lives prolonged. Based upon the contents in the tissue engineering technology, a small portions of healthy tissue, either from patients or donors, are needed, so that tissue cells can be cultured profusely in vitro, and seeded into a dissoluble porous scaffolds; thus, with the three-dimensional framework of said scaffolds, the tissue cells are to adhere thereto and grow thereon. Later on the tissue cells in time grow and form three-dimensional tissue blocks, which then are implanted back to the areas needed repair. In accordance with histology, a block of tissue contains specific compositive cells, and the three-dimensional extracellular matrix (ECM) is to cover the areas between cells. The ECM not only sustains the framework of cells, but also manifests the specific functions of such tissue. Take the cartilage tissue culture for example, for the three-dimensional culture of the cartilage tissue in vitro, it is proven that the three-dimensional culture of the cartilage tissue with the scaffold being agarose gel can sustain the original cell forms and functions in tissue and the mutated and transformed cartilage cells cultured two-dimensionally are to be recovered to the original cartilage cell forms under the three-dimensional culture with the scaffold being agarose gel. For simulating the framework of ECM, various materials are developed, e.g., collagen or poly (glycolic co-Lactic) acid (PLGA), as well as various structures, e.g., fiber-mesh or porous artificial scaffolds. However, the most serious drawback for the aforementioned technology is that, when tissue cells are cultured in large quantity in the two-dimensional culture dish, the phenomenon of dedifferentiation, due to the process of culturing the tissue with three-dimensional alignment in a two-dimensional space, is to occur on those proliferated cells, thus the original forms and functions of cells are to be lost.

Furthermore, the seeding of cells is also a problem difficult to overcome. The pore diameters on the porous scaffolds should be larger than the diameters of the cells to provide cells with enough space to be developed into tissue, thus when the mixture of cells and the culture medium is seeded into the porous scaffold, cells are to overflow out of the chamber for it is difficult to keep cells inside the scaffold. In order to solve the problem, there are two methods available: first is the static seeding method, with the characteristics described as follows. At first, the density of cells cultured is to be adjusted to that higher than $10^6$ cells/ml, and then, taking advantage of the water-containing nature of the porous scaffold, seeding cells are to be contained in the scaffold. After cells have all adhered to the scaffold, a large quantity of culture medium is added to start the culture process. Such method has the merits of knowing exactly how many the quantities of cells being seeded into the scaffold are, and high-density cells can be seeded into the scaffold. Nevertheless, the distribution of cells is still to be influenced by gravitational force, causing disproportional distribution between the upper layer and the lower layer of cells. Moreover, to prevent cells from overflowing, the volume of the culture medium mixed with cells is to be considerably limited, therefore the adhesion effect and the surviving rate shall both be taken into consideration. Another method is the dynamic seeding method of cells, with the characteristics described as follows. The spinner flask is used for spinning the water flow and thus cells are to be brought from the culture medium to the interior of the scaffold, a method that can obtain better adhesion rate of cells and better distribution of cells than that of the static seeding method. However, the drawbacks of the dynamic seeding method are as follows. The number of cells needed is higher, with the exact number of cells adhered in the interior of the scaffold being difficult to ascertain; also cells are seeded from the periphery, thus the density of cells in the periphery shall still be higher than that of cells in the interior. As a result, because cells in the periphery are having higher growth rate, a layer of hindrance is formed to prevent cells in the interior from exchanging nutrients, thus causing apparent disproportional proliferation between cells in the interior and those in the periphery of the scaffold.

SUMMARY OF THE INVENTION

One embodiment of the invention provides a novel and effective porous chamber to culture tissue in vitro, so as to avoid drawbacks like the phenomenon of dedifferentiation during the two-dimensional tissue culture in vitro, or disproportional growth of tissue cells in both the interior and the periphery of the scaffold.

Another embodiment of the invention provides a porous chamber for tissue culture in vitro comprising a main body made of porous biologically absorbable polymer material, comprising an inner surface surrounding a hollow cavity, the hollow cavity having an aperture opened at an upper surface of the main body, wherein the aperture is communicated with outside of the main body for seeding tissue blocks in the hollow cavity; and an upper cover passing through the upper surface of the main body to seal the aperture to prevent the tissue blocks from outflowing.

The shape of the porous chamber (the main body) can be altered depending on actual needs, e.g., the shape of a cylinder, a cube or any other kinds of shape. The porous chamber is made of absorbable polymer material, including polyglycolic acid (PGA), polylactic acid (PLA), poly (glycolic co-Lactic) acid (PLGA), polyanhydrides, polycapralactone, polydioxanone and polyorthoester, wherein the better material for the porous chamber is PLGA. The porous chamber is characterized in that at least one hollow cavity is included in the porous chamber for the purpose of containing the tissue blocks seeded inside. The diameters of the tissue blocks seeded are larger than the pore diameters of the scaffold in the periphery of the hollow cavities in the chamber, so as to prevent the tissue blocks from overflowing. The method for tissue culture in vitro of the present invention is to partially digest the tissue blocks via enzyme, and then seed the tissue blocks into the hollow cavity of the porous chamber, thus enabling the tissue to grow three-dimensionally inside-out toward the surrounding pores, and proliferating new tissue with the original form of the tissue, a method that cultures tissue needed in vitro by using the smallest quantity of tissue within the shortest period of time.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings, which are given by way of illustration only, and this are not limitative of the present invention, wherein.

DETAILED DESCRIPTION OF THE PREFERRED EMBODIMENTS

Figure 1:
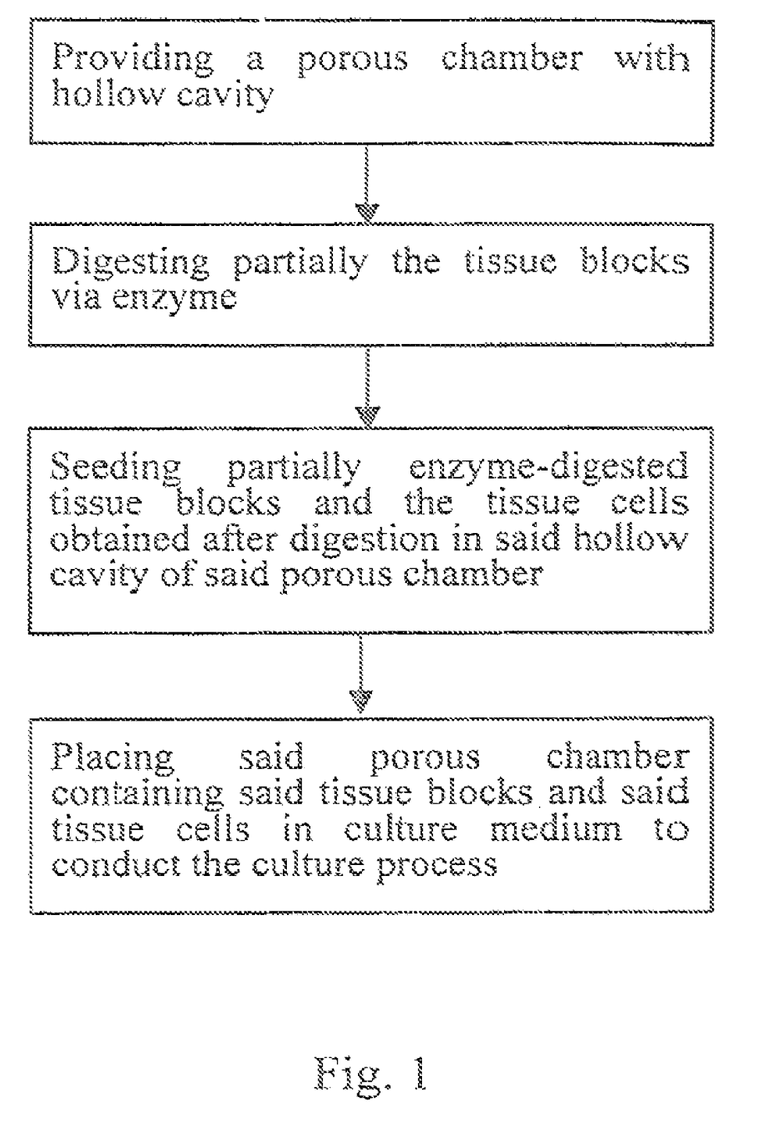
FIG. 1 shows the flowchart of the method for tissue culture in vitro of the present invention.
Figure 2:
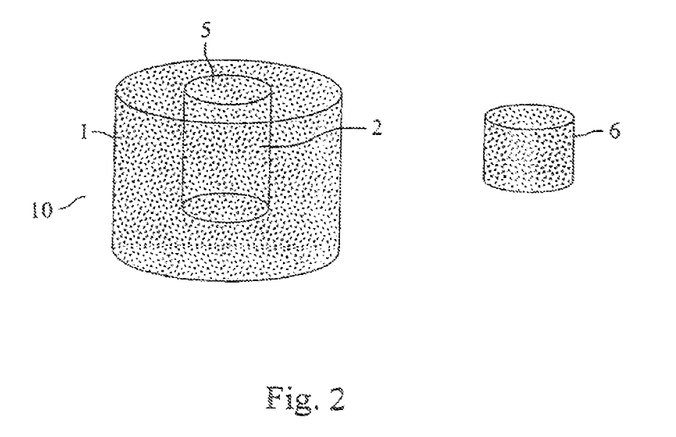
FIG. 2 shows the structural view of the porous chamber having hollow cavity of the present invention.
Figure 3:
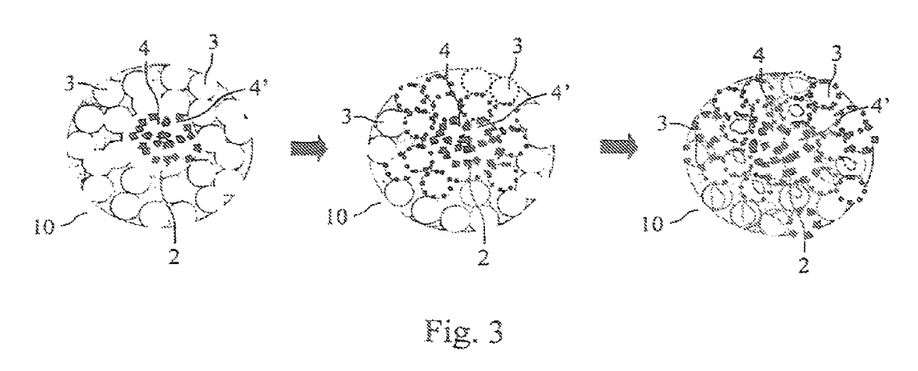
FIG. 3 shows the growing condition of the tissue in the porous chamber having hollow cavity of the present invention.

Please first refer to FIG. 1. The main object of the present invention is to provide a method for tissue culture in vitro, mainly comprising steps as follows: providing a porous chamber having hollow cavity; digesting partially the tissue blocks via enzyme; seeding the partially enzyme-digested tissue blocks and the tissue cells obtained after digestion into the hollow cavity of the chamber; placing the porous chamber containing the tissue block and the tissue cells in the culture medium to conduct the tissue culture process. As shown in FIG. 2, the porous chamber 10 of the present invention comprises a main body 1; at least one hollow cavity 2 which, containing an aperture 5, is located in the interior of the main body 1; and an upper cover 6 used for covering the aperture 5 of the hollow cavity 2. The method of the present invention is to directly collect tissues, and after cutting tissue into pieces and digesting the surface cells thereof via enzyme, the tissue blocks are to be seeded into the hollow cavity 2 of the porous chamber 10, with the periphery thereof being made of porous material; after which the cover 6 is used for covering the aperture 5 of the hollow cavity 2 to prevent the tissue blocks from overflowing. The sizes of the tissue fragments being cut can be controlled through sifting, thus the sizes of all the fragments are to be larger than the apertures of the scaffold in the periphery of the hollow cavity 2 of the porous chamber 10. When the tissue blocks are stuffed into the hollow cavity 2 of the porous chamber 10, the tissue blocks shall be confined inside the interior of the chamber 10 without overflowing, for the apertures of the peripheral scaffold are smaller than the sizes of the tissue blocks. Therefore, as shown in FIG. 3, the interior of the porous chamber 10 (which is the hollow cavity 2) shall contain enzyme-digested high-density cell groups and tissue blocks, and during the process of culture, because the cell density in the interior of the porous chamber 10 is very high, the tissue cells are to clamber up toward the peripheral porous scaffold where the cell density is lower, expand and grow along the original tissue blocks structure to proliferate the new tissue 4' three-dimensionally inside-out toward the apertures 3 of the peripheral porous scaffold. Such a culture method is entirely like the tissue culture in vitro and is used by the way that new tissues are cultured directly from the original tissue forms, thus solving the problem emerged out of the conventional culture method regarding the phenomenon of dedifferentiation by two-dimensional culture; and also, by using the culture method of the present invention, tissue needed can be cultured in vitro by using the smallest quantity of tissue within the shortest period of time. The tissue blocks 4 can be of any kind of animal tissue, e.g., cartilage tissue or bone tissue. The diameters of the tissue blocks 4 are to be from 500 to 1000 µm. The shapes of the porous chamber 10 can be altered depending on actual needs, e.g., cylinder, cube or any other kinds of shape. The porous chamber 10 is made of absorbable polymer material, including polyglycolic acid (PGA), polylactic acid (PLA), poly (glycolic co-Lactic) acid (PLGA), polyanhydrides, polycapralactone, polydioxanone and polyorthoester, wherein the better material for the porous chamber is PLGA. The upper cover 6 is made of the material identical to that of the main body 1. The range of the pore diameters of the porous chamber 10 is from 50 to 500 µm. The culture method of the present invention shall be further elaborated through the embodiments as follows.

Embodiments

The method for cartilage tissue culture in vitro:

1. Preparing the Biologically Absorbable Porous Chamber 10 Having hollow Cavity 2

The dissoluble polymer material chosen in this embodiment is the PLGApolymer prepared through ring scission polymerization (the molecular weight of polymer is approximately 200,000). By crushing the block-shaped PLGA polymer material in the crushing machine, the polymer particles with diameters ranging from 177 to 250 µm are to be obtained after sifting through the sifting net having 60 to 80 meshes. The water-soluble material chosen to add in the scaffold for creating the porous structure is sodium chloride particles with the diameters of approximately 250 µm; acetone is chosen to be the organic solvent used for dissolving polymer particles. The PLGA polymer particles and the sodium chloride particles, based on the weight ratio of 10/90, are to be well-proportionally mixed through way of spinning, following which the PLGA polymer particles and the sodium chloride particles are to be poured into a round-shaped filtering flask having 7 mm diameter with the lower end thereof connected to an exhaust device and then tightly compressed; at this time the organic solvent acetone is to be poured into the mixture of particles and the particles are dipped in acetone. And then the exhaust valve is to be turned on to produce a negative pressure downward to extract superfluous solvent out, and enable the dissolved polymer particles to adhere to one another, after which the deionized water is poured in on top of the filter and at the same time the exhaust valve is turned on to bring a large quantity of water flow through the material, the polymer particles are dialyzed and solidified, and the sodium chloride particles in the interior are washed out by water. Then the solidified polymer particles are to be taken out from the filter to be placed into a large beaker containing deionized water; while under normal room temperature, water shall be changed every six hours; also the solidified polymer particles are to be immersed and washed by water for a day by way of spinning, thus the remaining solvent and salt particles are to be washed out, following which the solidified polymer particles are to be heated and dried in the 50° C. vacuum oven for a day, then the porous scaffold with 90 vol % porosity rate is to be obtained having the pore diameters from 150 to 350 µm and pores connected with one another. The porous chamber 10 with hollow cavity 2 prepared in the embodiment is in the shape of a cylinder with 7 mm diameter and 9 mm height cut by scalpels, and a hollow cavity with 3 mm diameter and 6 mm height is scooped in the interior of the scaffold, then a cylindrical cork with 3 mm diameter and 3 mm height is cut (the upper cover 6 shown in FIG. 2), so as to seal the hollow cavity 2 when stuffed with tissue blocks inside. After completing the preparation of the porous chamber 10, the porous chamber 10 is to be immersed in the 75% alcohol for 6 hours for disinfection, and then the alcohol is to be replaced by a large quantity of sterile phosphate buffered saline (PBS) solution.

2. The Processing of the Experiment Group

Figure 4:
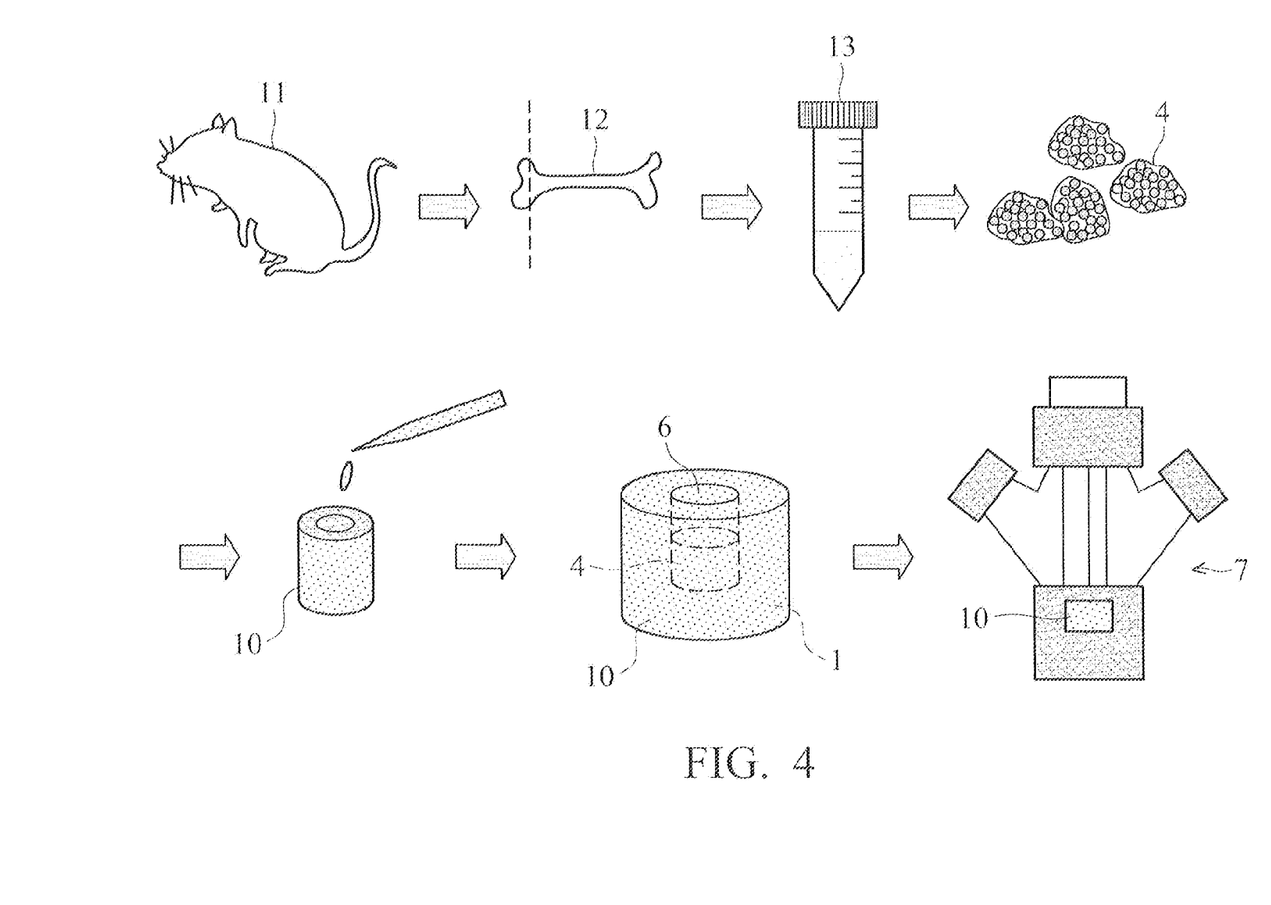
FIG. 4 shows a flowchart regarding the method for tissue culture in vitro of experiment group in the embodiment of the present invention.

First, as shown in FIG. 4, cartilage tissue is obtained from femur 12 of a mouse 11 two to four days after birth using micro-device, with the skins and periosteum on the surface thereof being discarded, and then femur 12 is to be dipped into DMEM without adding fetal calf serum (FCS); afterwards the femur 12 is to be taken out at laminar flow to be placed in a 15 ml centrifuge tube for washing by adding 10 ml of PBS solution, a process that is to be repeated twice. After washing, the femur 12 is to be poured into a 10 cm culture-dish, and then the joint cartilage is to be disintegrated and cut into pieces with a pair of autoclaved tissue scissors, with the sizes of the tissue blocks 4 being controlled with the range between 400 and 800 µm by using sifting net having 20 to 40 meshes. Fragments of the tissue blocks 4 after being cut are to be collected into the 15 ml centrifuge tube, and the PBS solution is poured in for the purpose of washing, a process that is to be repeated three times. After washing, the fragments of the cartilage tissue blocks 4 are to be rid of the PBS solution, and 5 ml of the collagenase (1 mg/ml PBS solution) is added; afterwards they are to be placed in an incubator with 37° C. for two hours, so as to ionize the cartilage cells on the surface. After digesting the cartilage blocks by using protease, they are to be placed in the centrifuge machine with the rotating speed of 1500 r.p.m. for 5 minutes of centrifuge, so as to disintegrate the protease and the cartilage blocks. Afterwards, the limpid protease supernatant is to be sucked up with the remaining fragments and cell tissue being washed twice with the PBS and centrifuged twice, so as to get rid of the remaining protease. The washed cartilage blocks and tissue cells are then to be stuffed into the hollow cavity 2 of the porous chamber 10, with the upper cover 6 covering thereon to prevent the cartilage blocks from overflowing.

3. The Processing of the Control Group

Figure 5:
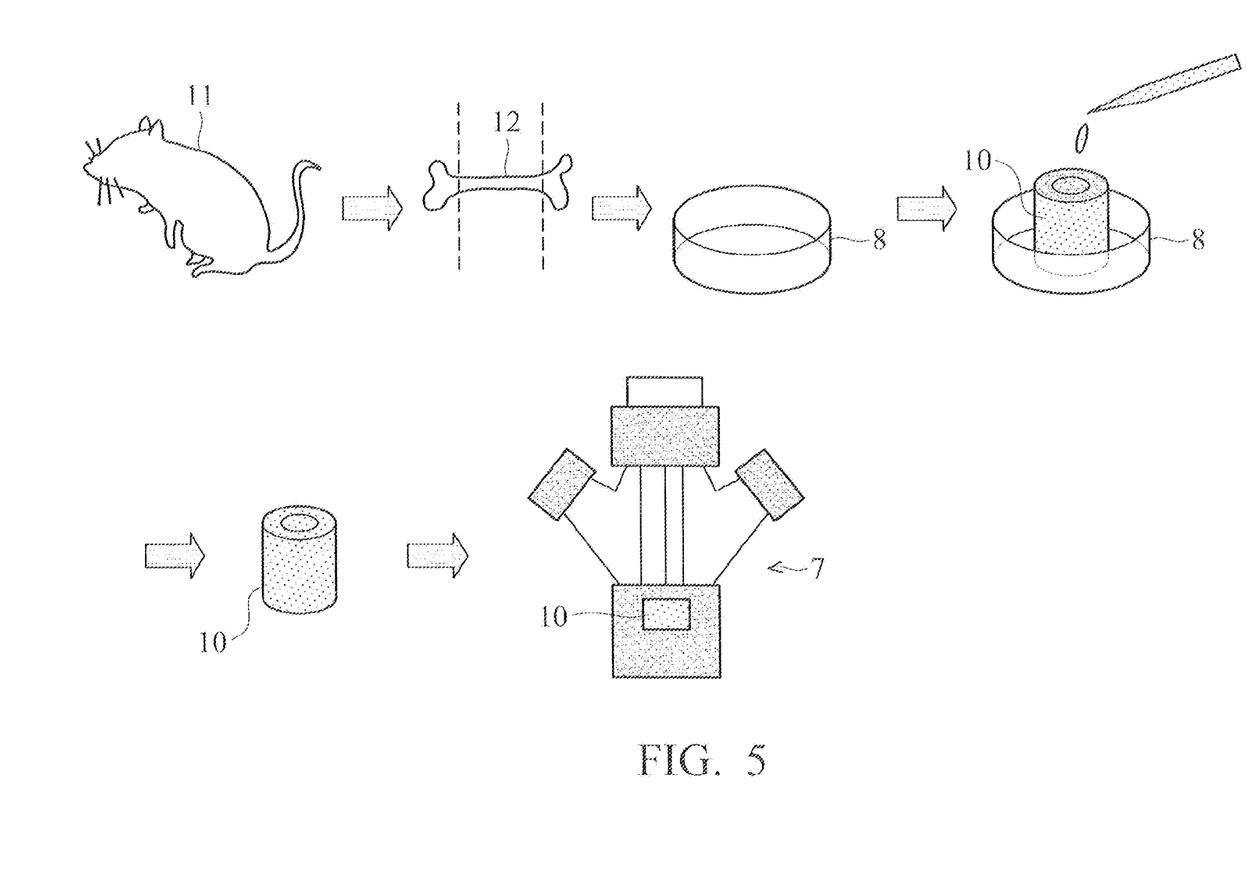
FIG. 5 shows a flowchart regarding the method for tissue culture in vitro of control group in the embodiment of the present invention.

First, as shown in FIG. 5, the identical culture method is used for the control group also, with the cartilage from the identical portion (femur 12) being used, and with the identical method of stripping the cartilage and cutting into pieces, after which the pieces are to be placed in the culture-dish 8, and then dipped in 5 ml of protease (1 mg/ml PBS solution) and hyaluronidase, and the culture-dish 8 is then to be placed in an incubator with 37° C. for 24 hours, so as to ionize all the cartilage cells. Based on previous research, cartilage with volume of 1 ml contains approximately $1.5 \times 10^7$ cartilage cells, thus, for the volume of the hollow cavity 2 of the porous chamber 10 being 0.02 ml, the number of cartilage cells needed to add is $3 \times 10^5$ in the control group. After centrifuging the cells needed to add, the number of cells is calculated by using cell counting plate, after which cells are to be added into the hollow cavity 2 of the porous chamber 10 (the volume of the added cell solution is 200 µl); to prevent cells from overflowing, the upper cover 6 is to be used to cover thereon, and then the porous chamber 10 is to be placed in the culture-dish 8, which is then to be placed in a moisturized incubator with 37° C. for 6 hours to enable cells to adhere thereon.

4. The Joint Processing of the Experiment Group and the Control Group

After the tissue cells of both the experiment group and the control group have been added into the porous chamber 10, the porous chamber 10 containing tissue cells are to be placed in the spinning flask 7 containing cell culture medium, as the final step shown in FIG. 4 and FIG. 5. The cell culture medium is of a DMEM culture medium containing 10% wt of FCS; with the nutrients for each chamber being 3 ml per day, the used culture medium is to be regularly replaced with fresh culture medium according to culture time, with the culture environment being an incubator with 37° C. containing 5% of $CO_2$. During the process of culture, the porous chamber 10 is to be taken out from the incubator at different culture time to be washed by using the PBS solution, and then to be dipped in the PBS solution containing 4% of formalin to fixate the test specimen, which is then to be cut first by way of paraffin embedding slide, and then dyed by way of hematoxylin-eosin stain, so as to observe the result of the cartilage tissue growth.

5. Result

Figure 6:
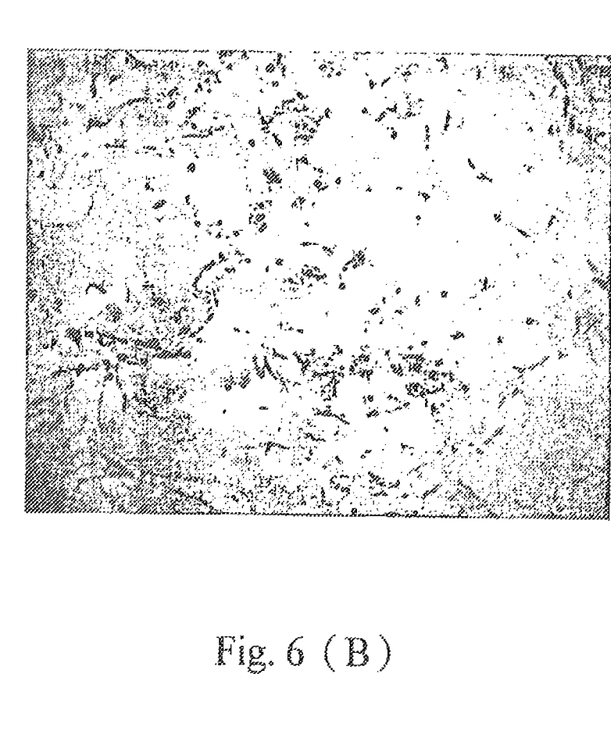
FIG. 6(A) shows a photograph regarding the growing condition of tissue and cells in the periphery of the stuffed cartilage tissue in the hollow cavity two weeks after culturing the cartilage tissue of the experiment group in the embodiment of the present invention.
FIG. 6(B) shows a photograph regarding the growing condition of tissue and cells in the porous scaffold in the periphery of the hollow cavity of the chamber two weeks after culturing the cartilage tissue of the experiment group in the embodiment of the present invention.
Figure 7:
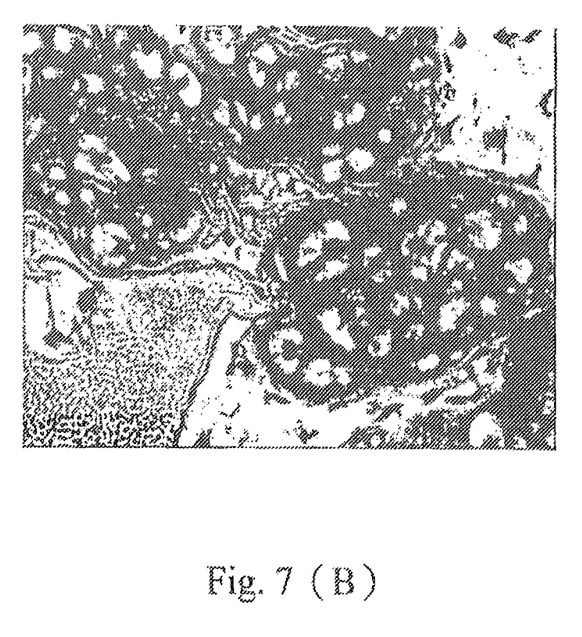
FIG. 7(A) shows a photograph (40 times magnification) regarding the growing condition of tissue and cells in the periphery of the stuffed cartilage tissue in the hollow cavity and in the porous scaffold in the periphery of the hollow cavity of the chamber four weeks after culturing the cartilage tissue of the experiment group in the embodiment of the present invention.
FIG. 7(B) shows a photograph (200 times magnification) regarding the growing condition of tissue and cells in the periphery of the stuffed cartilage tissue in the hollow cavity and in the porous scaffold in the periphery of the hollow cavity of the chamber four weeks after culturing the cartilage tissue of the experiment group in the embodiment of the present invention.

As shown in FIG. 6(A) and FIG. 6(B), after two weeks of using the culture method of the experiment group, it is to be observed that there can be found newly proliferated cartilage tissue 9 in pores surrounding the hollow cavity of the porous chamber, which grow inside-out directly from the periphery of the cartilage blocks seeded toward the peripheral pores, as shown in FIG. 6(A); also pores from other portions of the chamber, it is to be observed, are filled with cells proliferating inside-out from the middle, as shown in FIG. 6(B). FIG. 7(A) and FIG. 7(B) show the result after four weeks of culture, after which plenty of newly proliferated cartilage tissue 9 can be found not only in pores surrounding the hollow cavity, but also in pores from other portions, as shown in FIG. 7(A), and, with higher degree of magnification, plenty of cartilage cell lacunae can be found in the cartilage tissue, as shown in FIG. 7(B), wherein the cartilage cells have already begun to divide and grow, thus forming the homologous cells, manifesting that the cartilage formed is of very active newly proliferated cartilage tissue, and numerous flat chondroblasts, surrounding the periphery of such a cartilage tissue, shall continue to expand the proliferation process.

Figure 8:
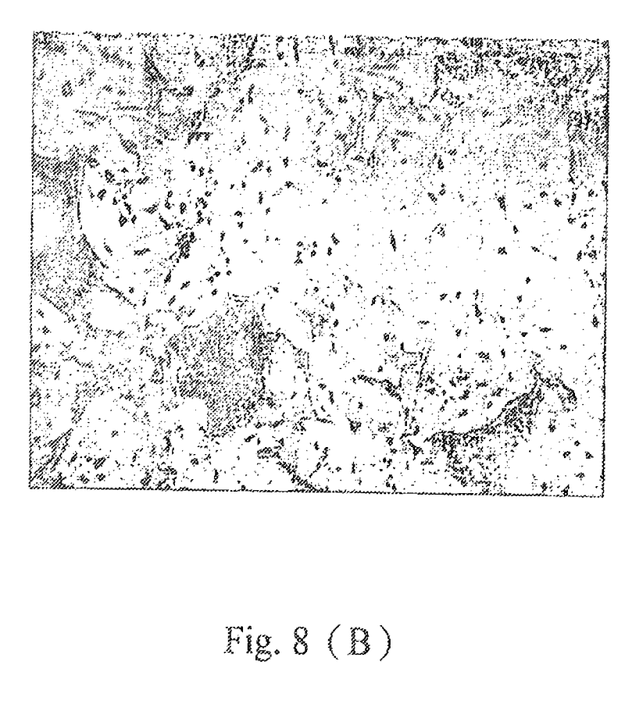
FIG. 8(A) shows a photograph (40 times magnification) regarding the growing condition of tissue and cells in the porous scaffold in the periphery of the hollow cavity of the chamber four weeks after culturing the cartilage tissue of the control group in the embodiment of the present invention.
FIG. 8(B) shows a photograph (200 times magnification) regarding the growing condition of tissue and cells in the porous scaffold in the periphery of the hollow cavity of the chamber four weeks after culturing the cartilage tissue of the control group in the embodiment of the present invention.

FIG. 8(A) and FIG. 8(B) both show the culture result by way of the control group, wherein, after culturing for four weeks, pores of the chamber with hollow cavity made of PLGA are full of cells, as shown in FIG. 8(A); to observe with higher magnification, it is found that the form of the newly proliferated cells is still the spindle-shaped fiber cartilage cells without forming the cartilage tissue, as shown in FIG. 8(B).

Figure 9:
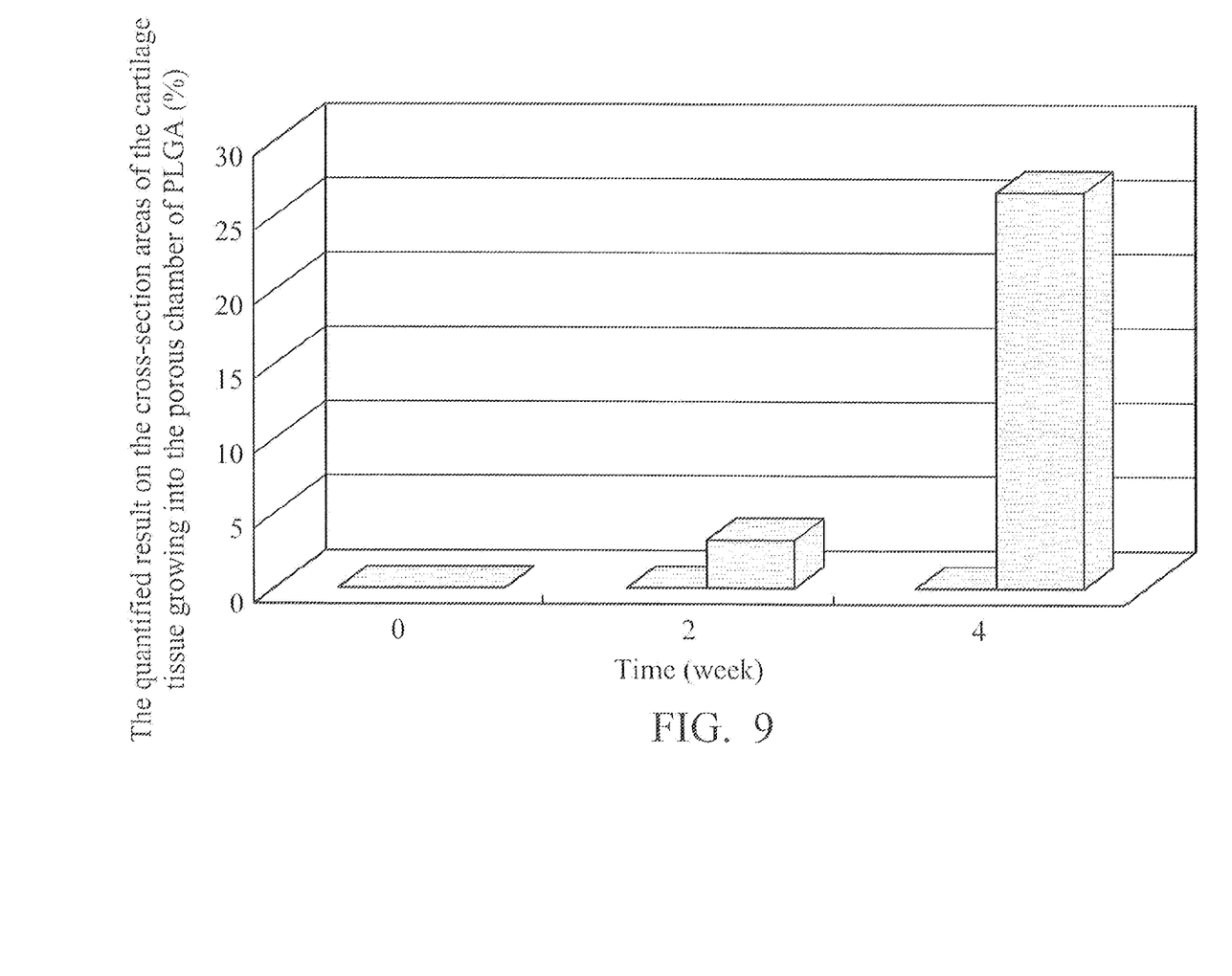
FIG. 9 shows a diagram of the quantified result on the cross-section areas of the cartilage tissue growing into the porous chamber made of PLGA in both the experiment group and the control group of the present invention.

FIG. 9 shows a diagram of the quantified result on the cross-section areas of the cartilage tissue proliferating in the pores on the periphery of the porous chamber in both the experiment group and the control group by using the microtissue image software. It is found, from the result shown in FIG. 9, that approximately 26% of the pore area can be filled by the cartilage tissue cultured with the method of the present invention, a huge difference comparing to the result of the control group, thus manifesting that numerous newly proliferated cartilage tissue can be cultured in vitro within a short period of time according to the culture method of the present invention.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A porous chamber for tissue culture in vitro, comprising:
    a main body made of porous biologically absorbable polymer material, comprising an inner surface surrounding a hollow cavity seeded with tissue blocks, the tissue blocks having a diameter of 500 to 1,000 μm, and the hollow cavity having an aperture opened at an upper surface of the main body, wherein the aperture is communicated with outside of the main body for seeding tissue blocks in the hollow cavity; and
    an upper cover passing through the upper surface of the main body to seal the aperture to prevent the tissue blocks from outflowing, and wherein a diameter of the upper cover is approximately the same as a diameter of the hollow cavity.

2. The porous chamber for tissue culture in vitro as claimed in claim 1, wherein the shape of the main body is cylindrical or cubic.

3. The porous chamber for tissue culture in vitro as claimed in claim 1, wherein the biologically absorbable polymer material is selected from the group consisting of polyglycolic acid (PGA), polylactic acid (PLA), poly (glycolic co-Lactic) acid (PLGA), polyanhydrides, polycaprolactone, polydioxanone, polyorthoester and collagen.

4. The porous chamber for tissue culture in vitro as claimed in claim 1, wherein the upper cover is made of the same porous material as that of the main body.

5. A porous chamber for tissue culture in vitro, comprising:
    a main body made of porous biologically absorbable polymer material, comprising pores distributed over an entire main body and an inner surface surrounding a hollow cavity seeded with tissue blocks, the tissue blocks having a diameter of 500 to 1,000 μm, and the hollow cavity having an aperture opened at an upper surface of the main body, wherein the aperture is communicated with outside of the main body for seeding tissue blocks and cells obtained from the tissue block after digestion with enzymes; and
    an upper cover passing through the upper surface of the main body to seal the aperture, wherein the diameters of the pores of the porous biologically absorbable polymer material are smaller than the diameters of the tissue blocks and larger than the diameters of the cells to prevent the tissue blocks from outflowing and to enable the cells to grow three-dimensionally inside-out toward the peripheral of the main body through the pores, and wherein a diameter of the upper cover is approximately the same as a diameter of the hollow cavity.

6. The porous chamber for tissue culture in vitro as claimed in claim 5, wherein the shape of the main body is cylindrical or cubic.

7. The porous chamber for tissue culture in vitro as claimed in claim 5, wherein the diameters of the pores of the porous biologically absorbable polymer material range from 50 to 500 μm.

8. The porous chamber for tissue culture in vitro as claimed in claim 5, wherein the biologically absorbable polymer material is selected from the group consisting of polyglycolic acid (PGA), polylactic acid (PLA), poly (glycolic co-Lactic) acid (PLGA), polyanhydrides, polycaprolactone, polydioxanone and polyorthoester.

9. The porous chamber for tissue culture in vitro as claimed in claim 5, wherein the upper cover is made of the same porous material as that of the main body.

10. The porous chamber for tissue culture in vitro as claimed in claim 5, wherein the enzyme comprises collagenase, hyaluronidase, trypsin or protease.

11. The porous chamber for tissue culture in vitro as claimed in claim 1, wherein the tissue blocks comprise cartilage tissue or bone tissue.

12. The porous chamber for tissue culture in vitro as claimed in claim 5, wherein the tissue blocks comprise cartilage tissue or bone tissue.

* * * * *

UNITED STATES PATENT AND TRADEMARK OFFICE
CERTIFICATE OF CORRECTION

PATENT NO.       : 7,767,445 B2                                      Page 1 of 1
APPLICATION NO.  : 11/808117
DATED            : August 3, 2010
INVENTOR(S)      : Chun-Jen Liao et al.

It is certified that error appears in the above-identified patent and that said Letters Patent is hereby corrected as shown below:

ON THE TITLE PAGE:

Please insert the following section:

--(30)        Foreign Application Priority Data

Dec. 10, 2001      (TW)      90130491--

Signed and Sealed this

Thirtieth Day of November, 2010

David J. Kappos
*Director of the United States Patent and Trademark Office*